Figure 1:
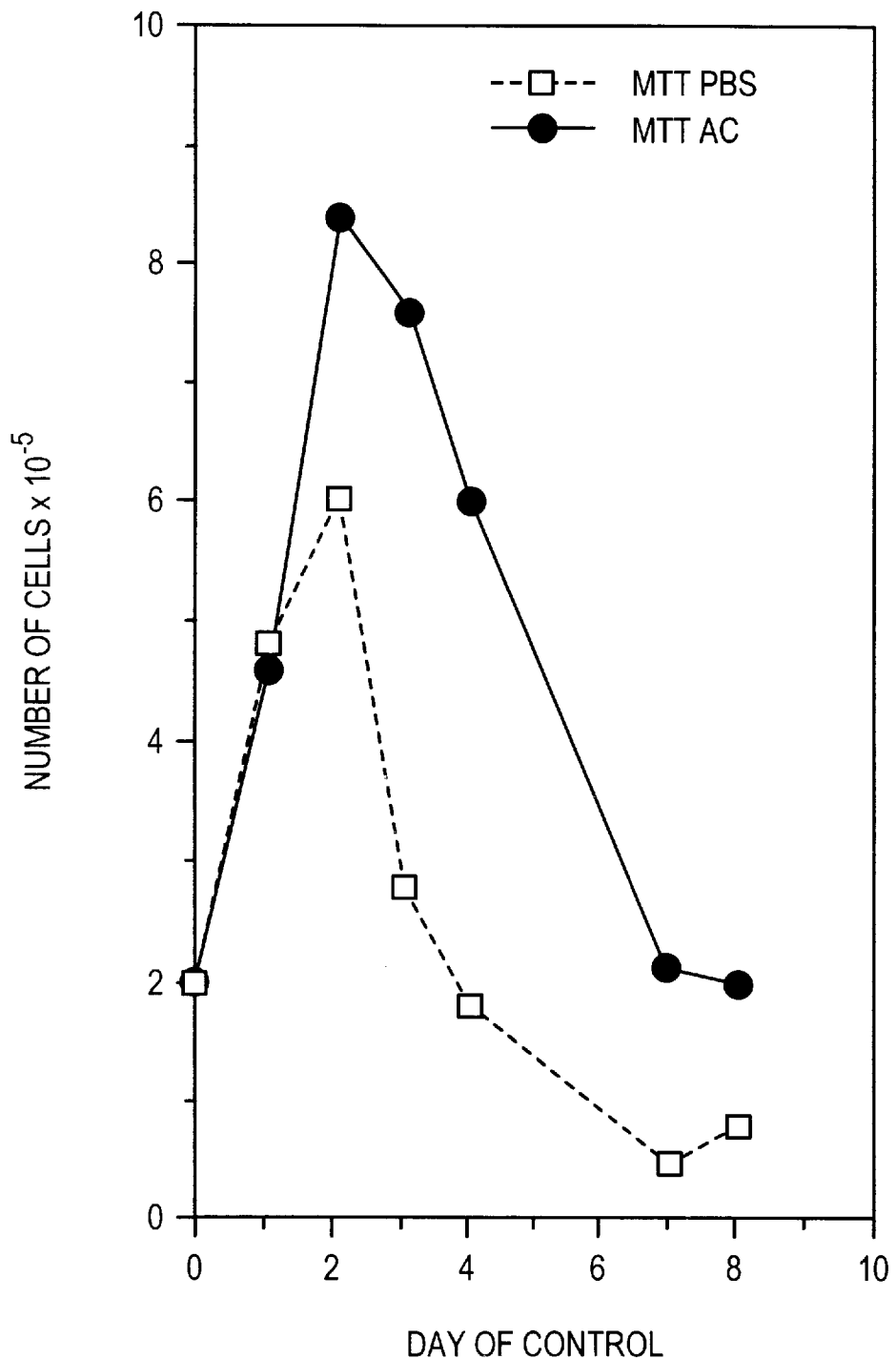

United States Patent [19]
Perrin et al.

[11] Patent Number: 5,891,475
[45] Date of Patent: Apr. 6, 1999

[54] PARTICULATE VECTOR AND PHARMACEUTICAL COMPOSITION CONTAINING IT

[75] Inventors: Pierre Perrin, Villiers-Sous-Grez; Daniel Samain, Toulouse; Nathalie Castignolles, Paris, all of France

[73] Assignees: Institut Pasteur, Paris; Biovectors Therapeutics S.A., Ramonville-Saint-Agne, both of France

[21] Appl. No.: 537,790

[22] PCT Filed: Apr. 21, 1994

[86] PCT No.: PCT/FR94/00452

§ 371 Date: Jan. 31, 1996

§ 102(e) Date: Jan. 31, 1996

[87] PCT Pub. No.: WO94/23701

PCT Pub. Date: Oct. 27, 1994

[30] Foreign Application Priority Data

Apr. 21, 1993 [FR] France .................................. 93 04698

[51] Int. Cl.$^6$ .................................. A61K 9/16; A61K 9/19
[52] U.S. Cl. .................................. 424/498; 428/403; 427/2.14
[58] Field of Search .................................. 424/484, 498; 428/403; 427/2.14

[56] References Cited

U.S. PATENT DOCUMENTS 5,151,264  9/1992  Samain et al. .................................. 424/1.1

FOREIGN PATENT DOCUMENTS 0 344 040  11/1989  European Pat. Off. .
90/09798   9/1990   WIPO .
92/21329   12/1992  WIPO .

Primary Examiner—Edward J. Webman
Attorney, Agent, or Firm—Burns, Doane, Swecker & Mathis, L.L.P.

[57] ABSTRACT

The invention relates to a particulate vector, characterized in that it comprises, from the inside to the outside, a non-liquid hydrophilic core, an external layer comprised of lipid compounds grafted on the core by covalent bonds. The invention also relates to a pharmaceutical composition containing such vectors, as well as to a process for enhancing the activity of the polypeptide cellular mediator.

18 Claims, 17 Drawing Sheets

PARTICULATE VECTOR AND PHARMACEUTICAL COMPOSITION CONTAINING IT

The present invention relates to a new type of particulate vector for the transport and presentation of molecules of active ingredients which are at least partially hydrophobic and which interact with specific cell receptors. It also relates to a process for enhancing and controlling the activity of such molecules, in particular of molecules of lymphokines.

The cytokines (also called lymphokines) constitute a group of proteins which play an important role in the regulation and the function of the immune system. They have pleiotropic actions and act by specific interaction with cell receptors with a very high affinity. Some are used or proposed as therapeutic agents (e.g. interferons, interleukin-2 . . . ). One of them, interleukin-2 (IL-2) is particularly representative of this family.

IL-2 is synthesized predominantly by the helper T lymphocytes (Th1) in response to a stimulation by the antigen presented by appropriate cells. It is involved in the development of the specific and nonspecific immune responses: it interacts with various cells in order to activate them (T and natural killer—NK—lymphocytes), in order to induce their proliferation and their differentiation (T, NK and B lymphocytes). IL-2 has antitumor properties: it can induce regression of various solid tumors, of melanomas, leukemias or of lymphomas and the like. IL-2 is also of interest in vaccinology: it enhances especially the protective power of certain viral (herpes, rabies . . . ) and bacterial (Haemophilus pleuripneumoniae) vaccines.

IL-1 has been proposed for protecting the myeloid cells against the cytotoxic effect of chemotherapy.

Hematopoietic growth factors of the G-CSF and GM-CSF type can be used in the treatment of certain types of leukopenia especially after chemotherapy.

The administration of γ-interferon appears to limit the phenomena of allergy by blocking the production of IL-4.

Nevertheless, these are molecules which are capable of taking part in a cascade of biological reactions, sometimes synergistically, and which are capable of bringing about disturbing side effects (fever, erythema, edema).

In addition their purification is difficult and they are often produced by genetic engineering and are therefore expensive.

It would therefore be desirable to be able to have a vector system which makes it possible to decrease the administered doses, through an increase in the observed activity for the same concentration of active molecule and through an extension of the duration of action over time.

Accordingly, the subject of the present invention is a particulate vector, characterized in that it comprises, from the inside to the outside,
  a nonliquid hydrophilic core,
  an external layer consisting of lipid compounds, grafted on the core by covalent bonds.

The core of this particulate vector has, preferably, a size of between 10 nm and 5 μm.

The transport systems described up until now have a structure mimicking that of the lipoproteins, in particular at the level of the external surface. This is the case especially for liposomes which consist of a lipid double layer surrounding an aqueous vacuole. This is also the case for the supramolecular biovectors (SMBV) described in patent EP 344 040, which contain an external layer of amphiphilic compounds.

Nevertheless, this type of structure is perhaps not capable of being used for certain classes of active ingredients, with which there is a risk of undesirable interactions occurring, leading to the disorganization of the vector and to the loss of its properties. In particular, for IL-2, no satisfactory transport system exists up until now.

One object of the present invention is therefore to provide an efficient vector having a simpler structure. Surprisingly, it was found that particles comprising only a hydrophilic core, preferably consisting of a matrix of naturally or chemically cross-linked polysaccharides or oligosaccharides, and of an external lipid layer, make it possible to bind active ingredients having a biological activity and to considerably increase the efficacy thereof.

The core may be nonionic or ionic.

An ionic core is obtained by grafting, onto the hydrophilic matrix, ligands carrying functional groups which may be positively or negatively charged. These functional groups may be chosen from the group comprising: phosphate, sulfate, carboxylic acid, quaternary ammonium, secondary amine or primary amine.

The ionic grafting should not be damaging to the stability or to the size of the polysaccharide matrix. These ligands will therefore be chosen preferably from biological molecules naturally present in the body, and coupled to the matrix via enzymatically hydrolyzable bonds.

When the ligands grafted onto the matrix are acidic compounds, they may be especially chosen from succinic acid, phosphoric acid, citric acid, glycine, alanine, glutamic acid, aspartic acid.

Succinic acid is a natural constituent of the body and is involved in the Krebs cycle. It is a dicarboxylic acid which can form with the hydroxyls of the polysaccharide matrix an ester bond easily biodegradable by virtue of the ubiquitous presence of succinylesterase in the body. The acid functional group which is not engaged in the ester functional group with the polysaccharide matrix therefore remains available to provide the ion-exchange properties.

It is also possible to graft onto the matrix monohydroxyls or monoamino acids, for example citric acid, short-chain amino acids and acidic amino acids.

According to another aspect of the invention, the ligands grafted onto the matrix are basic compounds, bound to the matrix by means of an acidic compound.

In order to obtain the biodegradable grafting of basic ligands, it is possible to use especially succinic acid between the polysaccharide matrix and a basic compound. One of the acid functional groups of succinic acid is used to produce a biodegradable ester functional group with the polysaccharide matrix and the other acid functional group is used to produce an ester or amide functional group with the basic compound.

Preferably, the basic ligands grafted onto the matrix are bifunctional compounds comprising an acylable functional group forming an amide or ester bond with an acidic compound bound to the matrix.

The acylable functional group is for example a hydroxyl functional group or a primary amine.

The other, nonacylated functional group is for example a primary, secondary or tertiary amine functional group or a quaternary ammonium.

The ligand may be especially chosen from choline, hydroxycholine, 2-(dimethylamino)ethanol and 2-(dimethylamino)ethylamine.

In a preferred embodiment, the external lipid layer consists of natural fatty acids. These natural fatty acids are bound only to the surface of the core by a regioselective acylation process which avoids derivatization within the bulk. This is obtained by carrying out the grafting reactions in an aprotic nonsolvent medium for the polysaccharides, which preserves the particulate hydrophilic structure of the core and ensures homogeneous distribution of the lipid constituents. The quantity of lipid reagent, for example of fatty acid chloride, for obtaining saturation conditions is therefore relatively low.

The level of acylation of the vector can thus be varied by performing one or more successive acylation cycles. The degree of acylation of the core plays a role in the properties of the vector and its capacity to bind, to release and to enhance the activity of the active ingredients.

The Applicant has shown that if the polysaccharide core alone can bind for example interleukin-2, practically no biological activity is observed when these cores charged with IL-2 are placed in an appropriate cell medium. On the other hand, maximum enhancement of the IL-2 activity is observed for particulate vectors comprising a core with a low acylation level.

The increase in the acylation level slightly decreases the activity enhancement phenomenon but prolongs the duration of this activity.

The particulate vector according to the invention can advantageously be freeze-dried. The freeze-drying is carried out in a hydrophilic environment which modifies the surface properties of the vector. One of the hypotheses, by which it is not at all intended to limit the invention, is that during the freeze-drying, a folding of the fatty acid chains occurs towards the inside of the structure, leaving a hydrophilic external surface. During use, the vector is rehydrated directly with the solution of the active ingredient to be transported.

The object of the invention is therefore also a particulate vector which comprises, in addition, molecules of at least one cellular mediator having both a hydrophobic character and an ionic character, of the type which acts via a membrane receptor; the said molecules are associated by hydrophobic interactions with the external layer of lipid compounds of the vector, and/or by ionic interactions at the core.

These cellular mediators may be polypeptides, glycosylated or otherwise, which play a role in the functioning of the immune system.

In all cases, the molecules of active ingredient associated with the external lipid layer must have a partially hydrophobic character. The Applicant has indeed demonstrated that interactions between the vector according to the invention and a cell mediator such as IL-2 are broken by the addition of a nonionic detergent of the Hecameg type (6-0-(N-heptylcarbamoyl)methyl-α-D-glucopyranoside). In addition, ionic interactions also occur between the core, which has an acidic character (especially by virtue of the grafting of phosphate radicals) and the basic functional groups of IL-2.

Among the molecules of cellular mediators for which the particulate vector is of specific interest, there may be mentioned cytokines which include a set of soluble mediators produced by the cells. They comprise the lymphokines or interleukins, which are secreted by immunocompetent cells which provide the interactions between the leukocytes, the monokines, the TNFs (or α and β tumor necrosis factors), the different interferons (α-, β- and γ-IFNs), G-CSF, M-CSF, GM-CSF and MIF.

Among the most suitable mediators, the activity of IL-2 is increased by the association with the particulate vectors according to the invention; IL-1, which possesses a membrane form of 23 kD and the 26 kD membrane form of TNF are particularly appropriate for the preparation of vectors according to the invention.

The acylation level varies so as to obtain the best interaction with the associated mediator molecules, which depends on the respective hydrophilicity/hydrophobicity ratios of the lipid crown and the active ingredient, taking into account the effect, of amplification or delay in the release, desired.

The subject of the invention is also pharmaceutical compositions containing particulate vectors according to the invention, charged or otherwise with molecules of cellular mediator, and a pharmaceutically acceptable vehicle.

The applications of the vectors and of the compositions according to the invention comprise the preparation of forms for in vivo administration of active ingredient. They also comprise the supplementation of media for in vitro culture of cell lines, producing for example a protein of interest.

Generally, one of the subjects of the invention is a process for enhancing the activity of a polypeptide cellular mediator which is at least partially hydrophobic, characterized in that
 a) a particulate vector is prepared which comprises from the inside to the outside
  a core consisting of a matrix of naturally or chemically cross-linked polysaccharides or oligosaccharides,
  an external layer consisting of natural fatty acids grafted onto the core by covalent bonds, at a variable level,
 b) optionally, the vector obtained is freeze-dried in a hydrophilic environment,
 c) the cellular mediator is associated with the vector via interactions which are at least partially hydrophobic.

The effect on the activity of the cellular mediator may especially comprise an increase in the intrinsic activity and/or an increase in the shelf life of the active ingredient associated with the vector according to the invention.

According to one of the aspects of the invention, the vectors, consisting of the cross-linked hydrophilic core preferably carrying ionic ligands and onto which the fatty acid residues are bound, also called "acylated nuclei", are freeze-dried. The charging with proteinaceous active ingredient is carried out by placing the freeze-dried acylated nuclei in contact with a limited quantity of proteinaceous aqueous solution of active ingredient, so as to bring about the formation of stable aggregates of vectors charged with active ingredient. These aggregates are then dispersed in an aqueous phase by dilution.

Other characteristics and advantages of the present invention will emerge upon reading the examples below.

In these examples, reference will be made to the following figures:

FIG. 1: Proliferation of CTLL cells in the presence of IL-2 mixed with acylated polysaccharide cores (batch 14): number of live cells (MTT counting).

Figure 2:
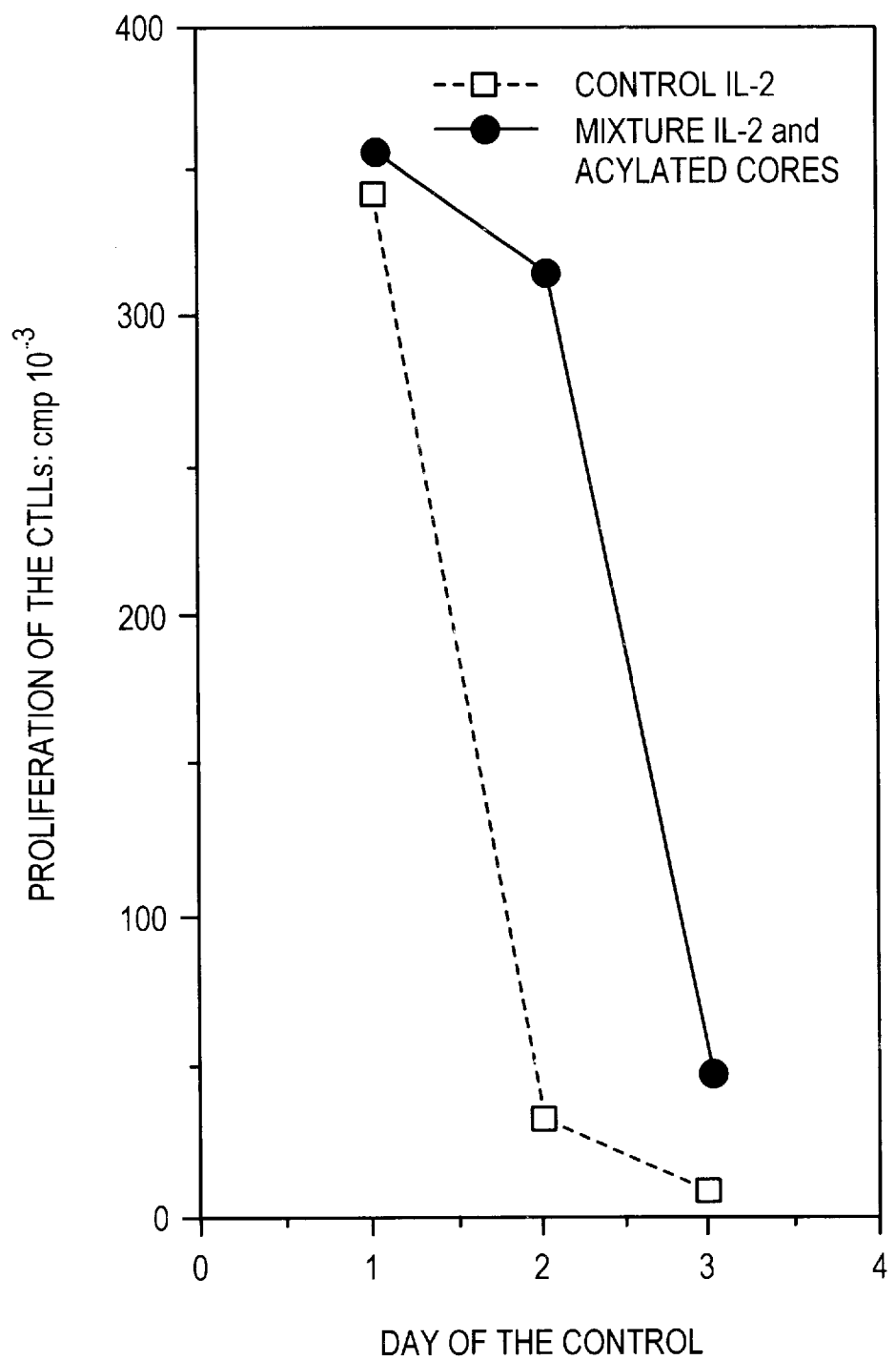

FIG. 2: Proliferation of CTLL cells in the presence of IL-2 mixed with the acylated polysaccharide cores: proliferative capacity of the cells.

Figure 3:
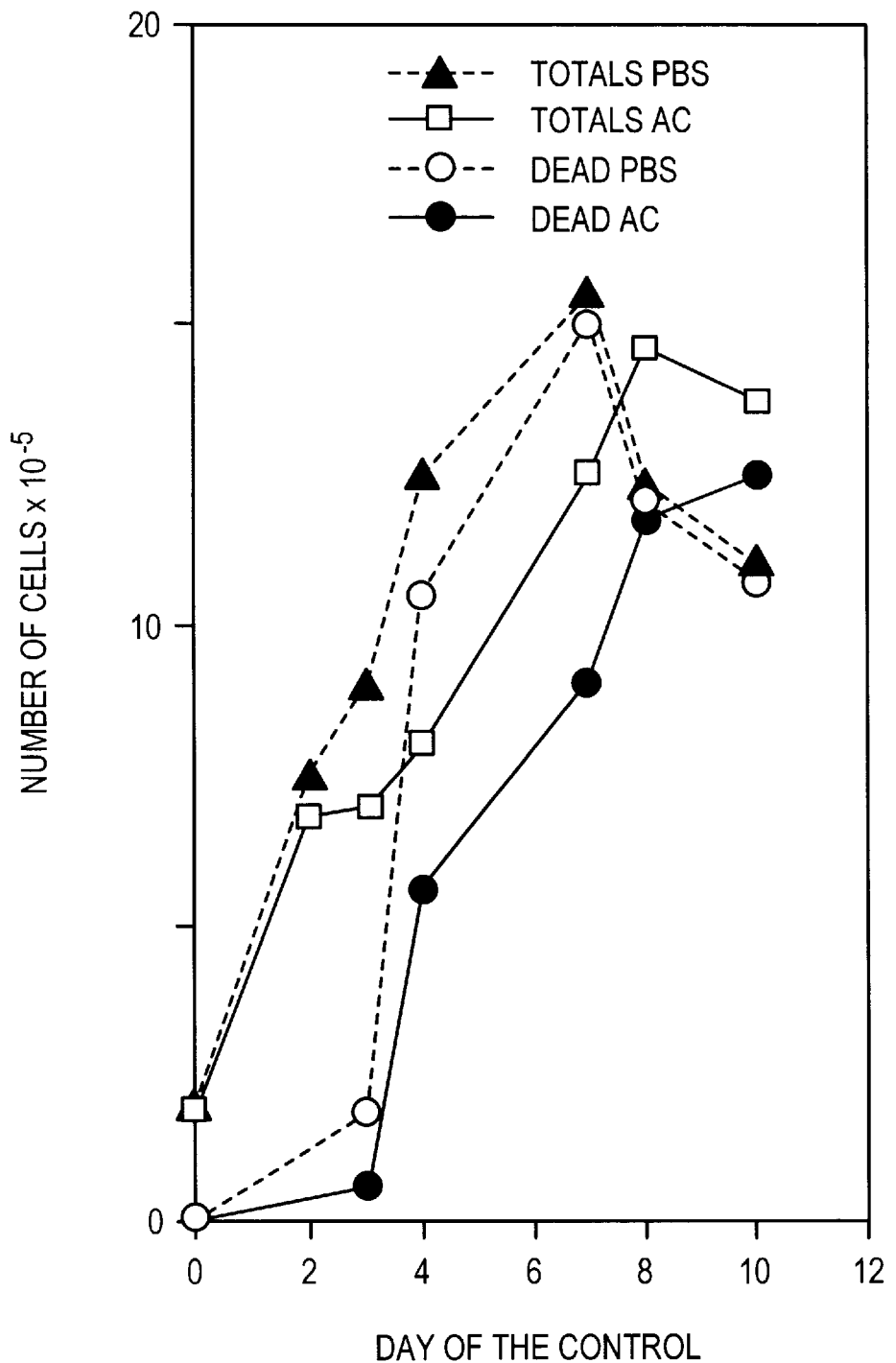

FIG. 3: Influence of the association of IL-2 with acylated polysaccharide cores on the proliferative activity of IL-2 dependent cells.

Figure 4:
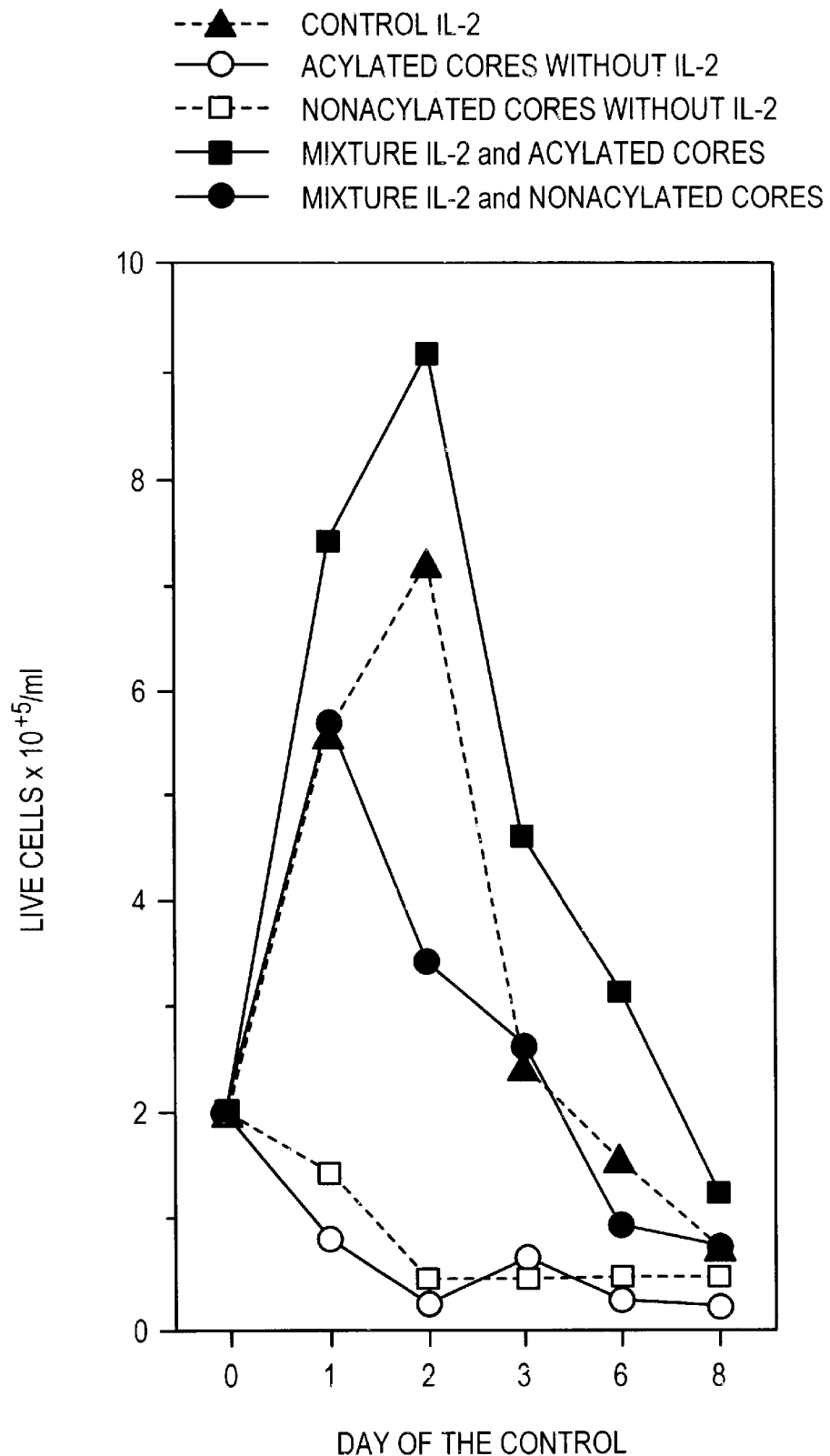

FIG. 4: Influence of the presence of acyl residues (AC batch 18) on the polysaccharide cores (PSC) on the enhancement of the properties of IL-2.

Figure 5:
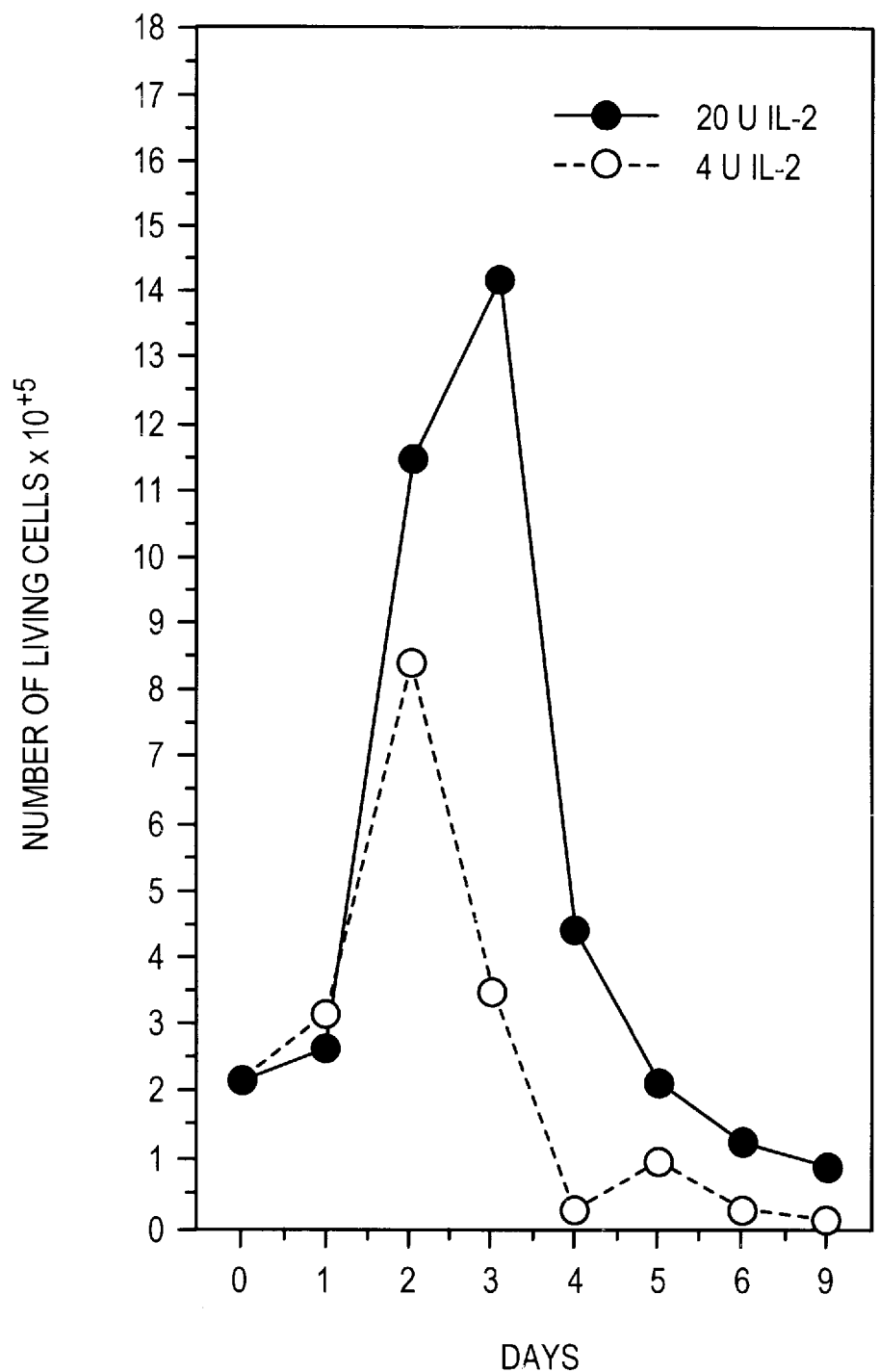

FIG. 5: Growth of CTLL cells in the presence of two quantities of IL-2 (4 and 20 U).

Figure 6A:
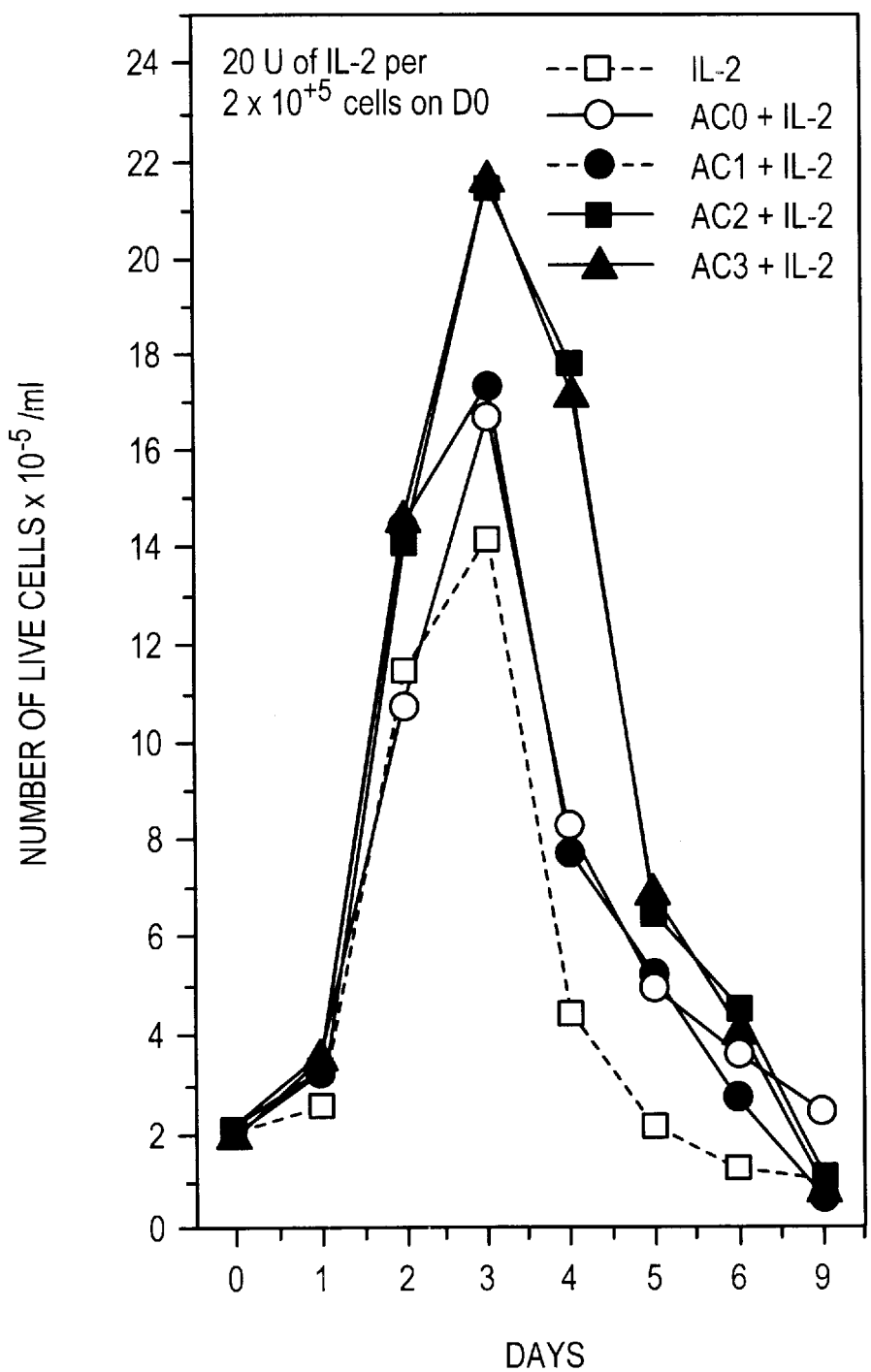

FIG. 6a: Influence of the number of acylations of the cores on their capacity to enhance the biological properties of IL-2: growth of the IL-2 dependent cells in the presence of 20 U of IL-2 mixed with variously acylated cores.

Figure 6B:
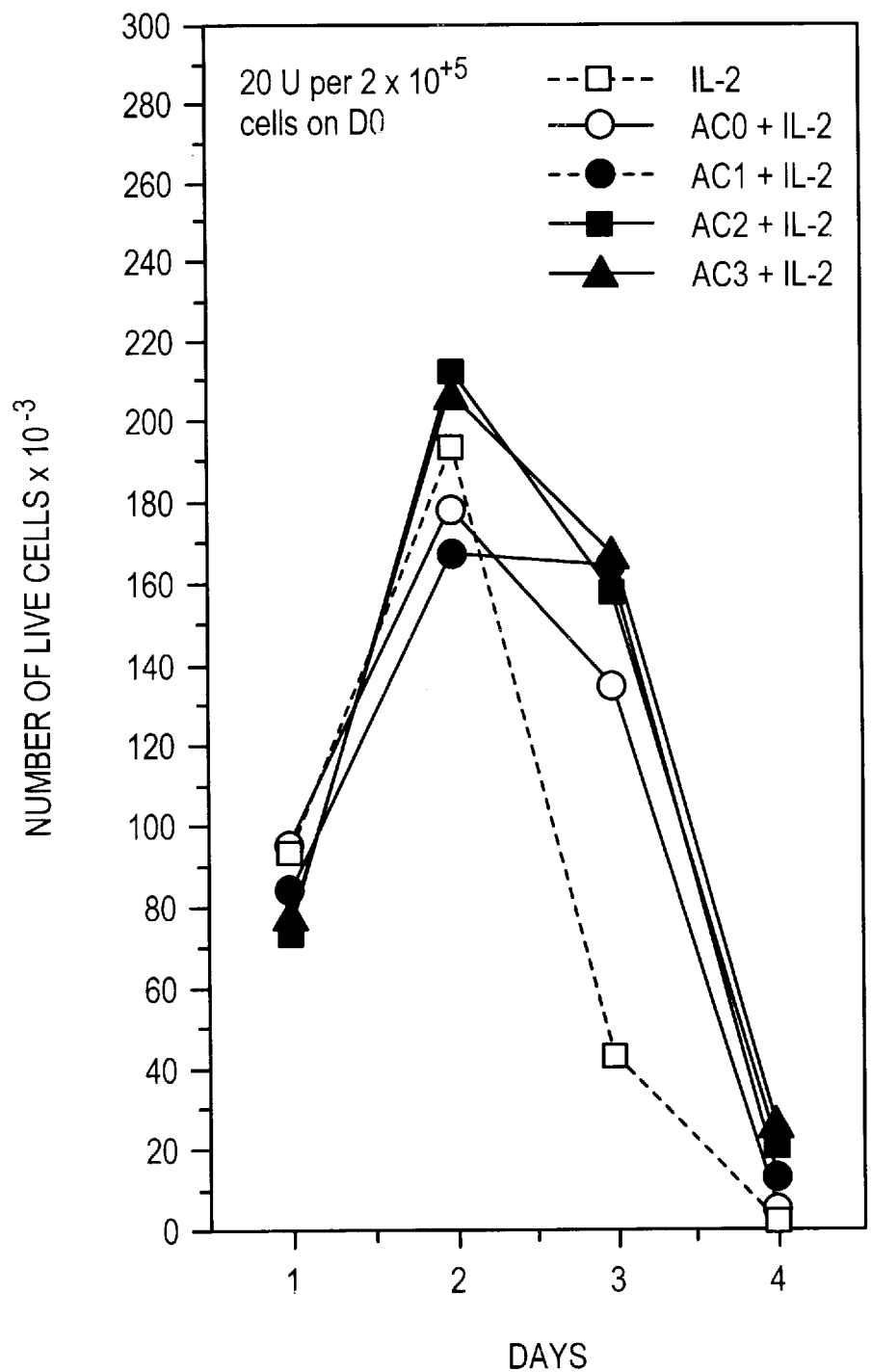

FIG. 6b: Influence of the number of acylations of the cores on their capacity to enhance the biological properties of IL-2: proliferative capacity of the IL-2 dependent cells.

Figure 7A:
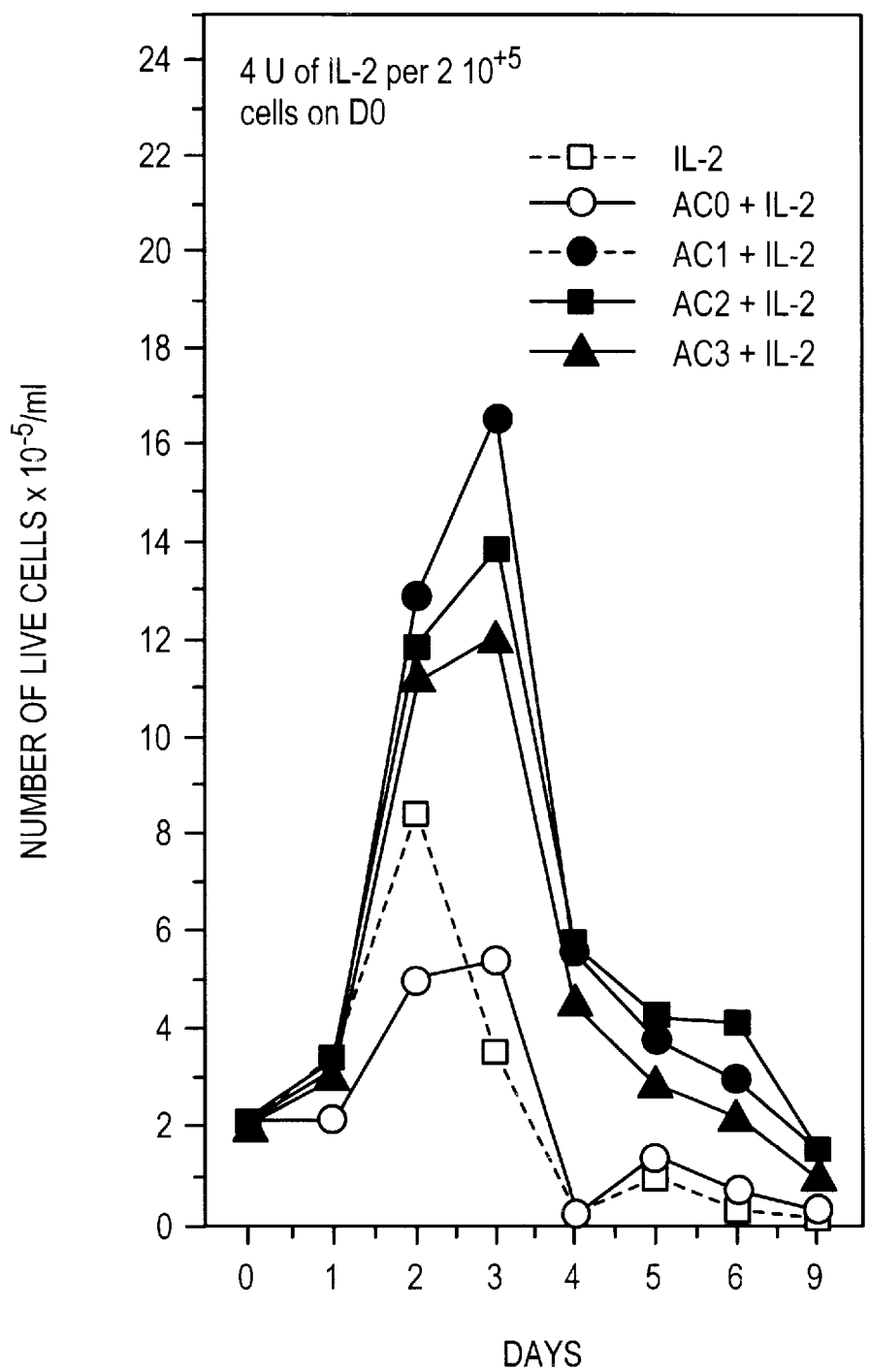

FIG. 7a: Influence of the number of acylations of the cores on their capacity to enhance the biological properties of IL-2: growth of the IL-2 dependent cells in the presence of 4 U of IL-2 mixed with variously acylated cores.

Figure 7B:
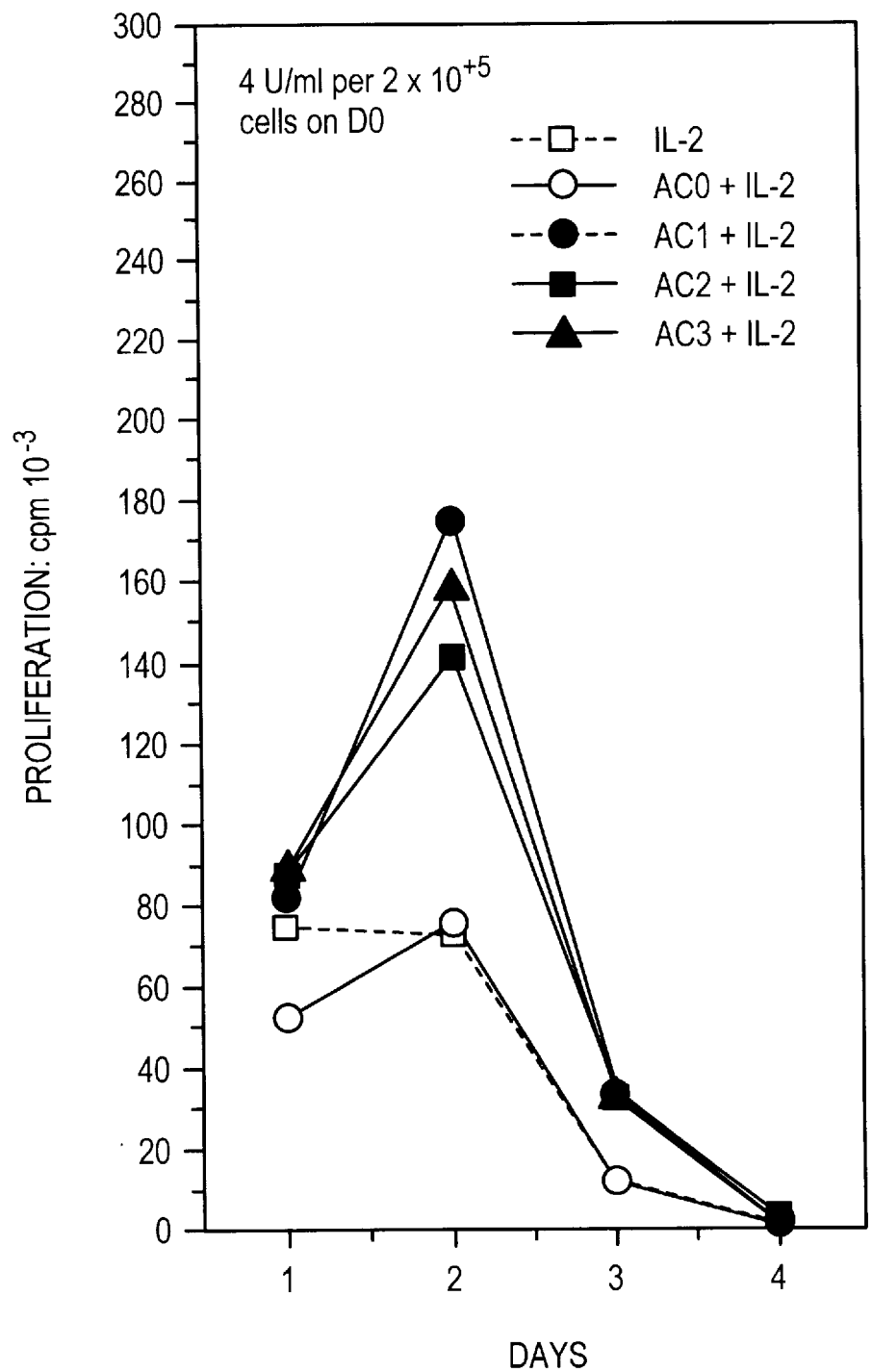

FIG. 7b: Influence of the number of acylations of the cores on their capacity to enhance the biological properties of IL-2: proliferative capacity of the IL-2 dependent cells.

Figure 8A:
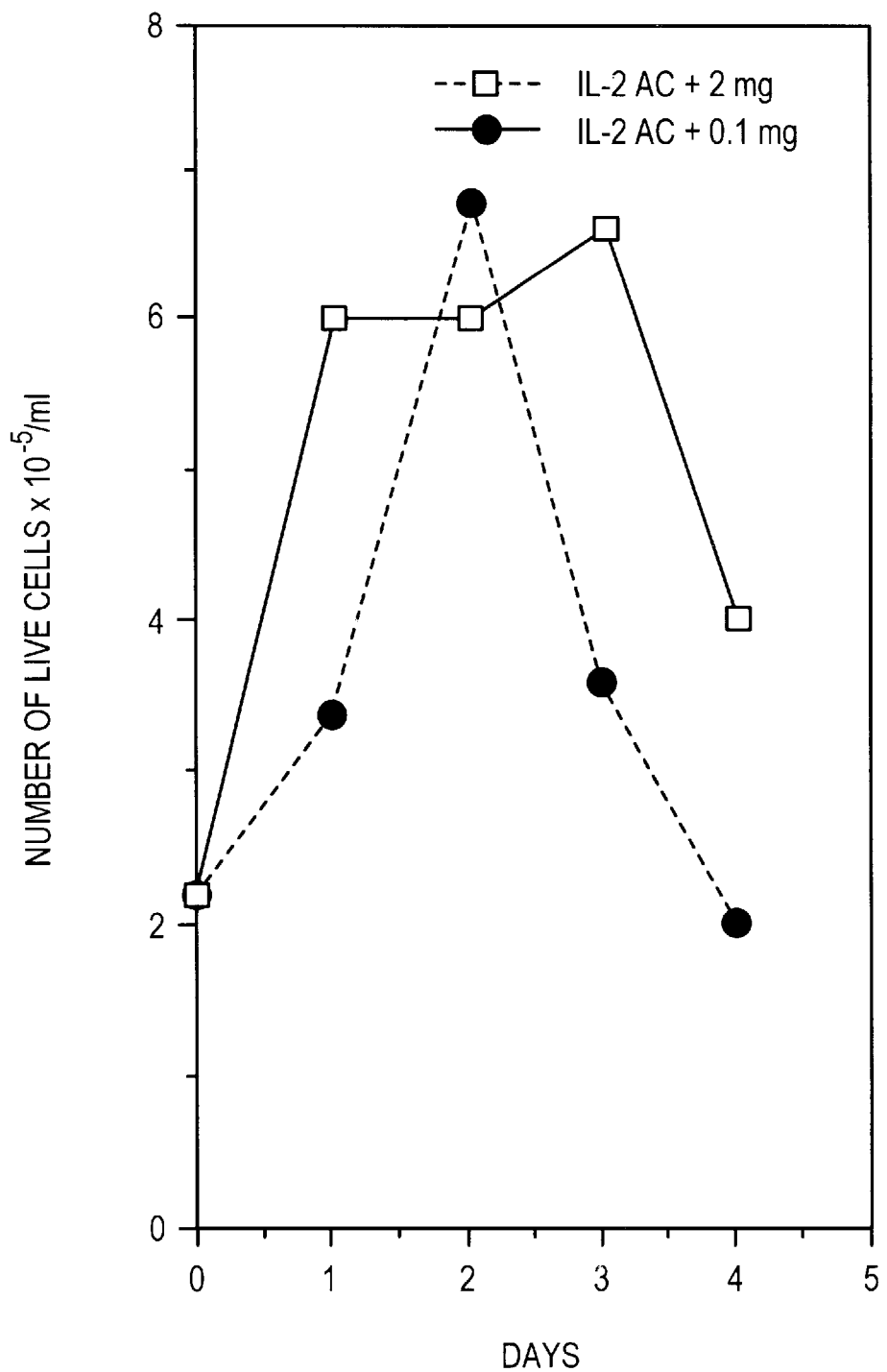

FIG. 8a: Influence of the quantity of cores on the biological properties of IL-2: growth of the IL-2 dependent cells in the presence of 0.1 mg and of 2 mg of acylated cores.

Figure 8B:
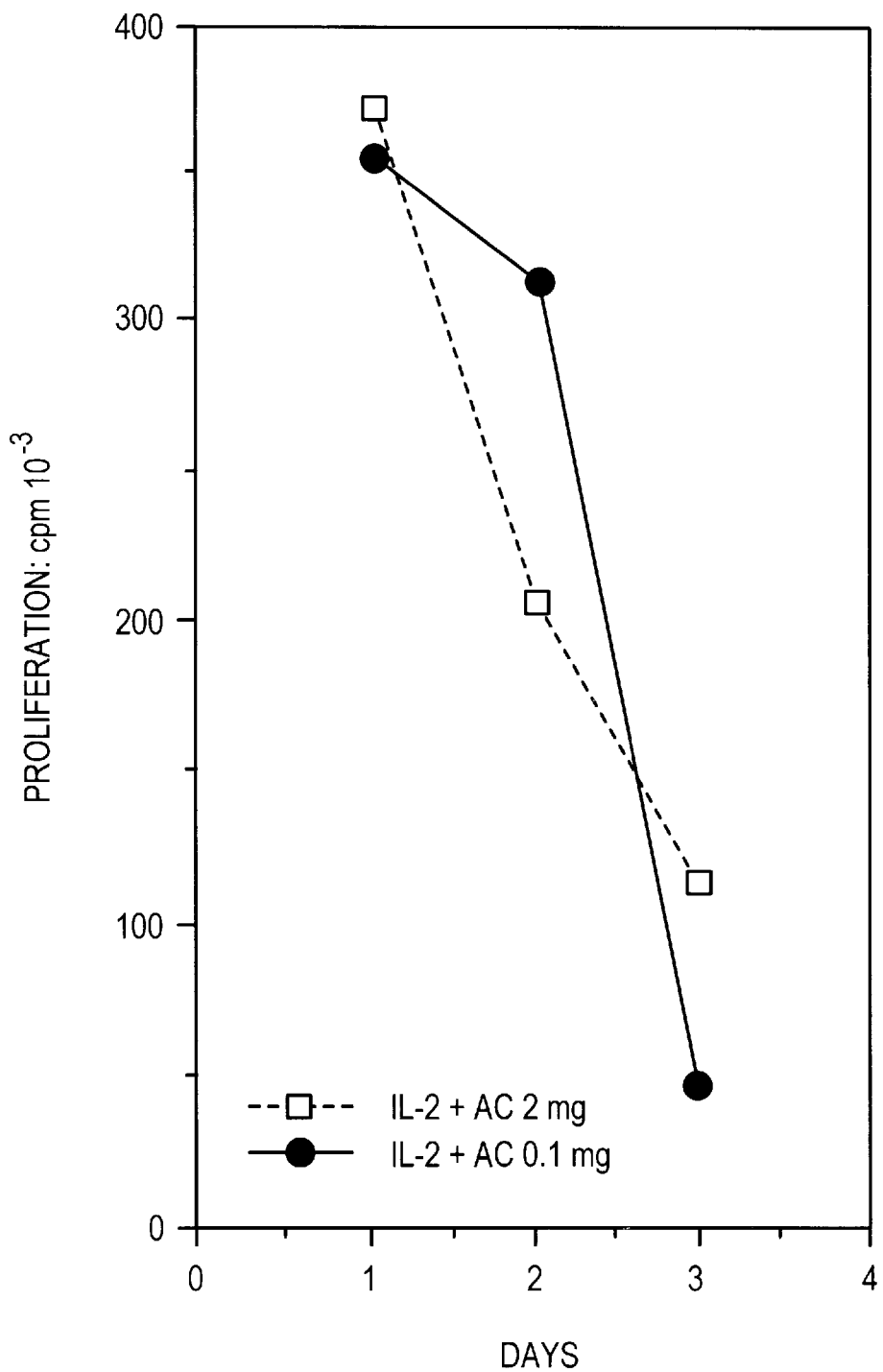

FIG. 8b: Influence of the quantity of cores on the biological properties of IL-2: proliferative capacity of the IL-2 dependent cells.

Figure 9:
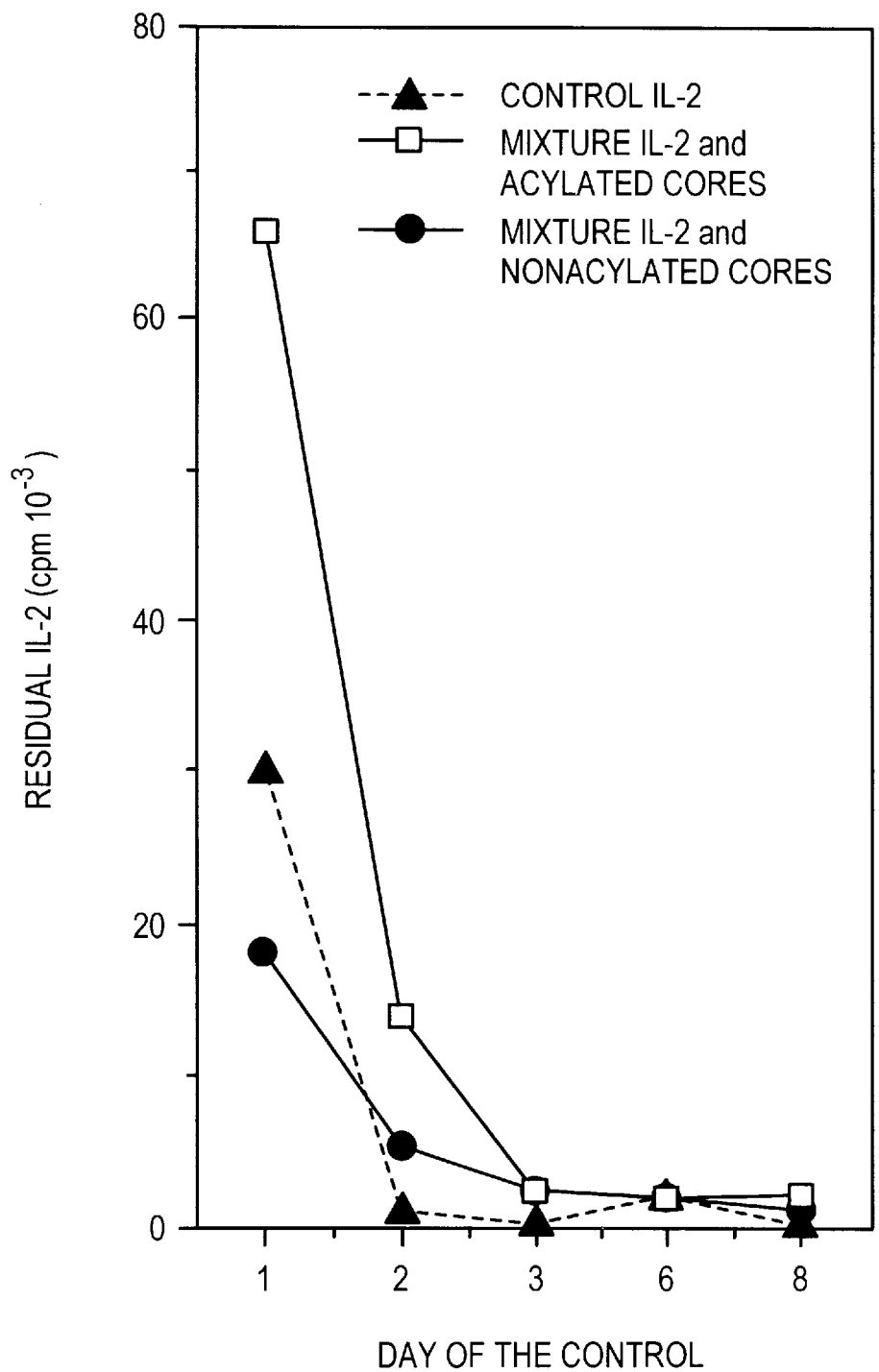

FIG. 9: Influence of the presence of acyl residues (AC batch 18) on the polysaccharide cores (PSC) on the enhancement of the properties of IL-2.

Figure 10:
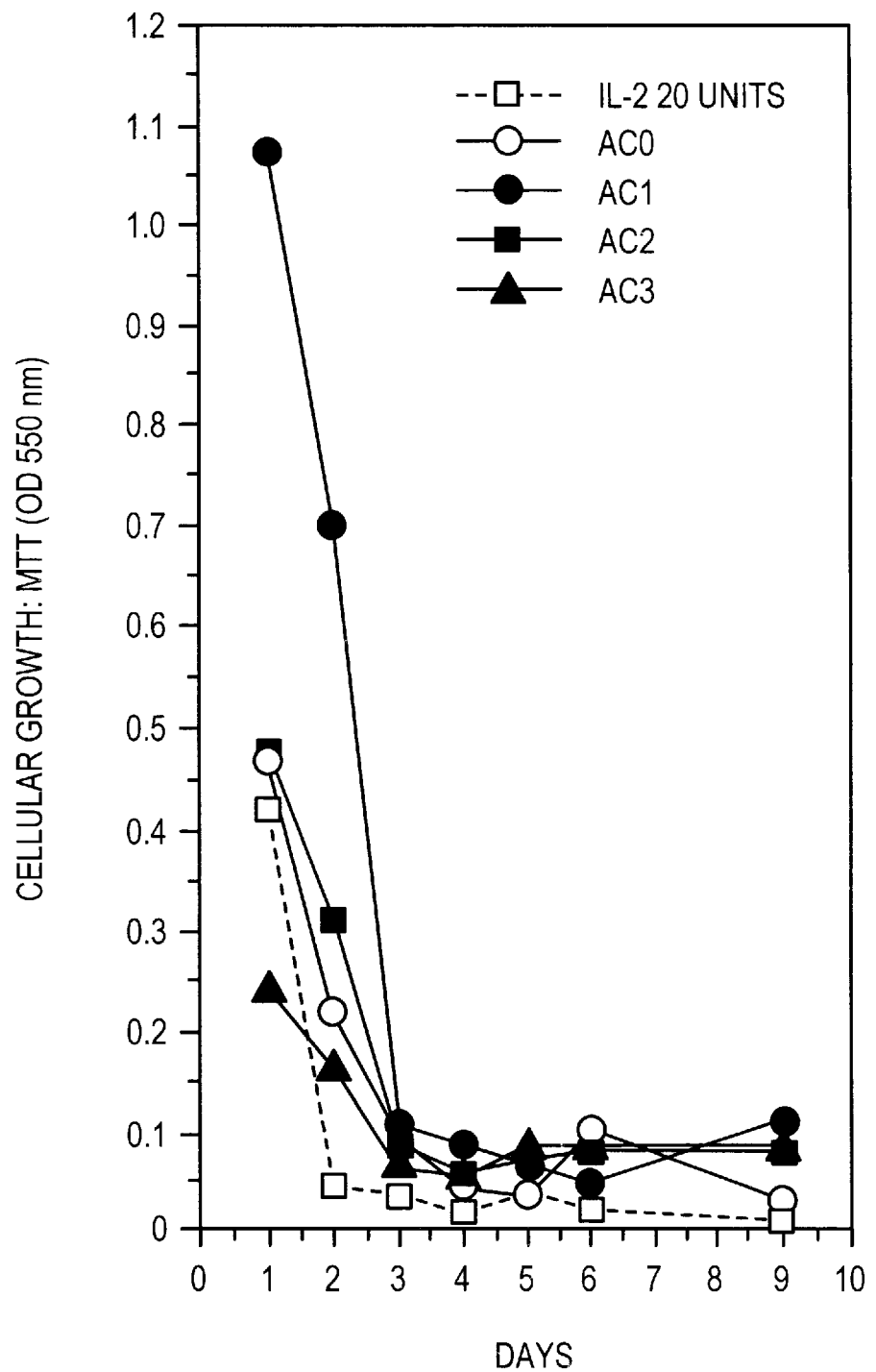

FIG. 10: Influence of the number of acylations of the PSCs on the stability and/or release of IL-2 into the culture medium: assay of residual IL-2 in the culture supernatants.

Figure 11:
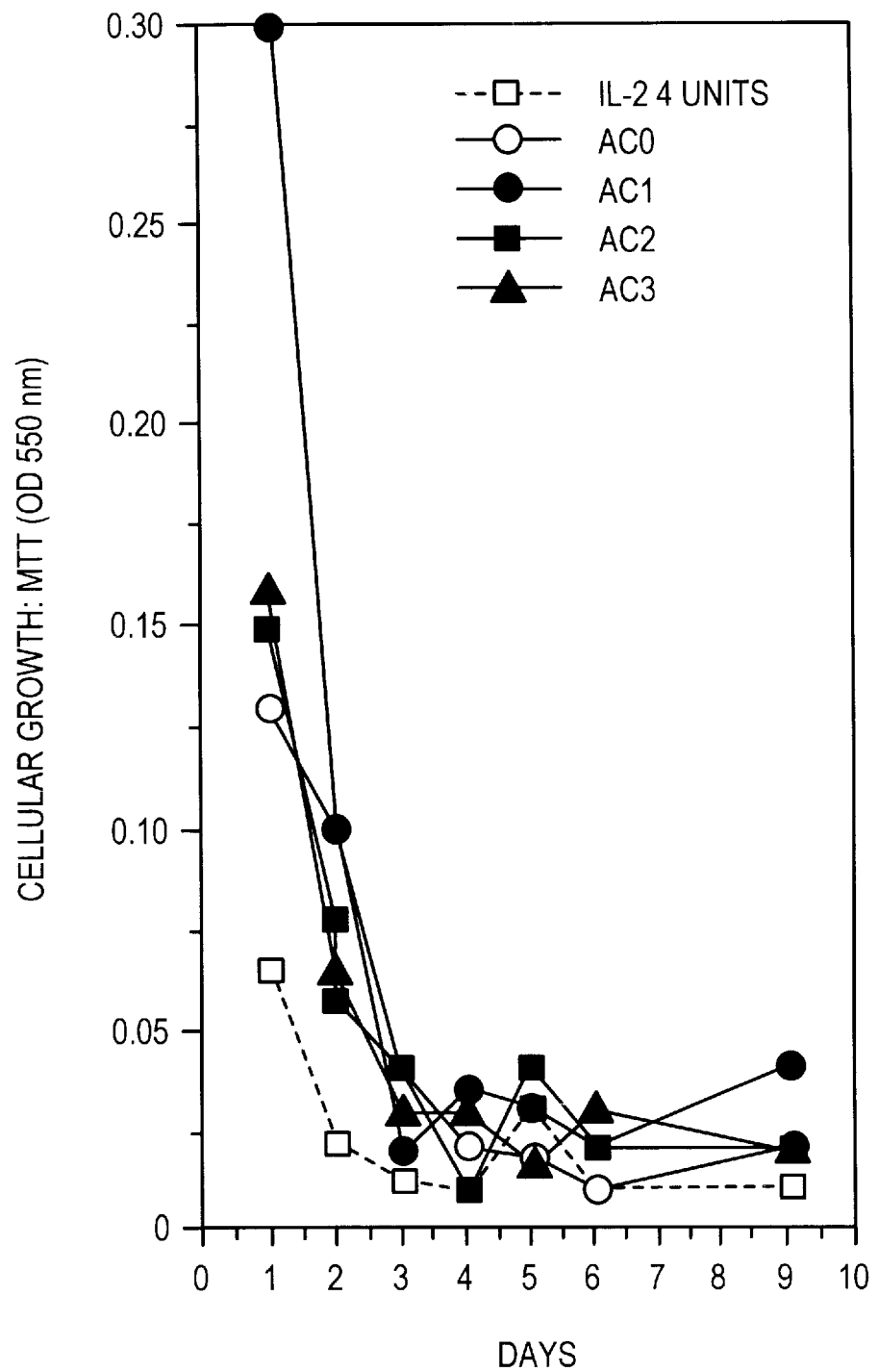

FIG. 11: Residual IL-2 in the culture supernatants.

Figure 12:
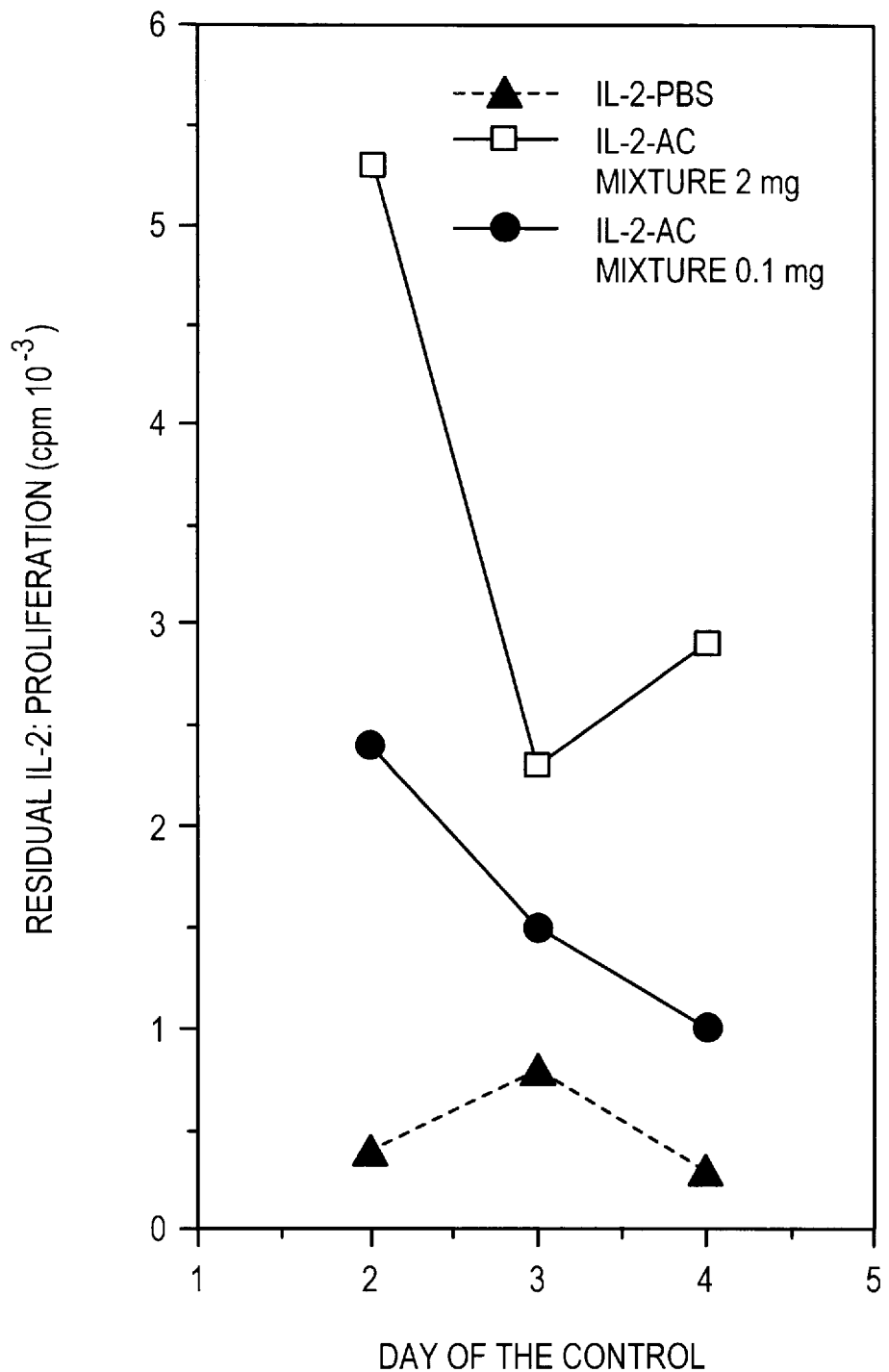

FIG. 12: Influence of the quantity of acylated polysaccharide cores on the quantity of residual IL-2 assayed in the culture supernatants of the CTLL cells.

Figure 13:
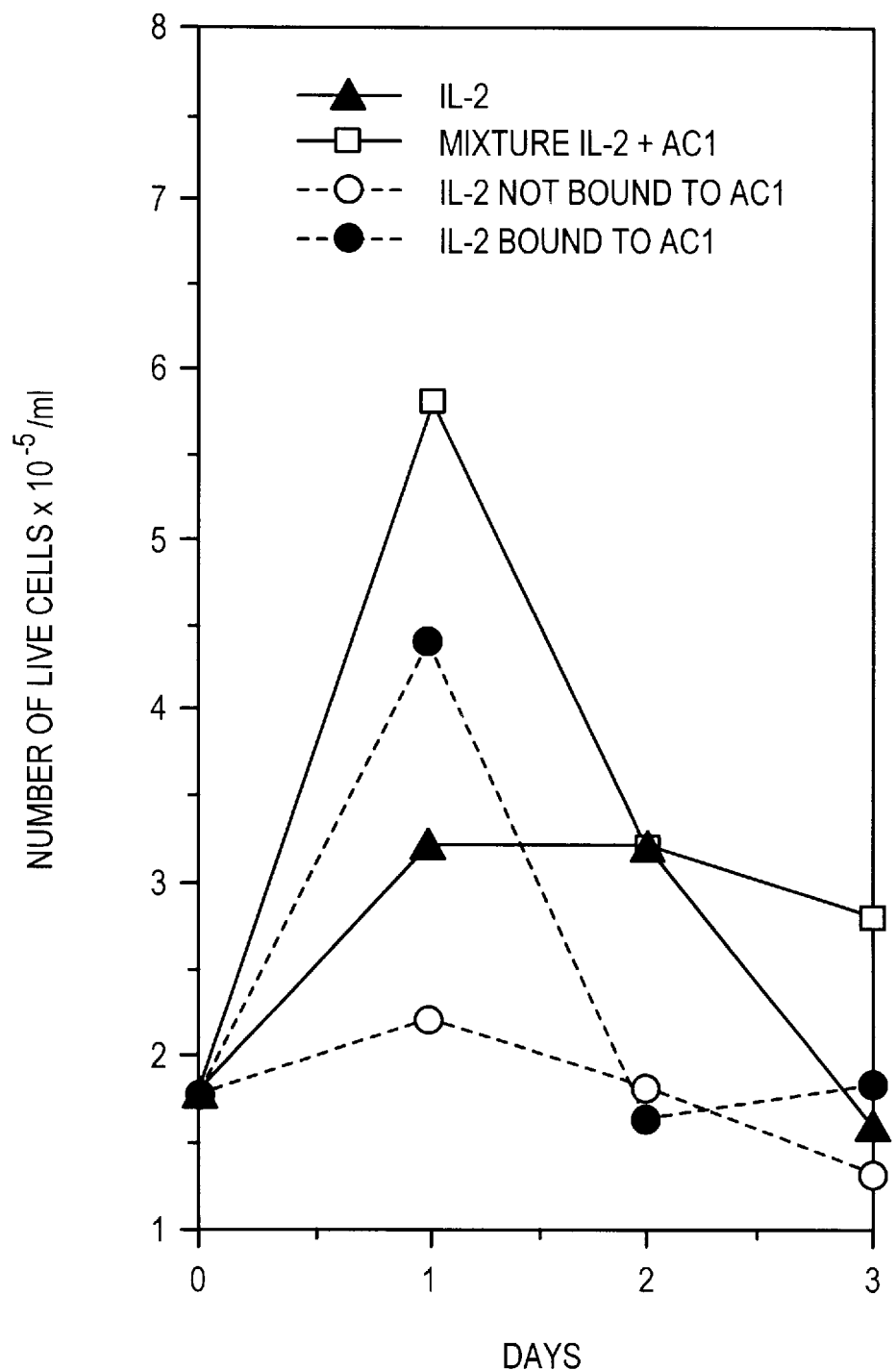

FIG. 13: Growth of the IL-2 dependent cells in the presence of IL-2 bound to the acylated cores.

Figure 14:
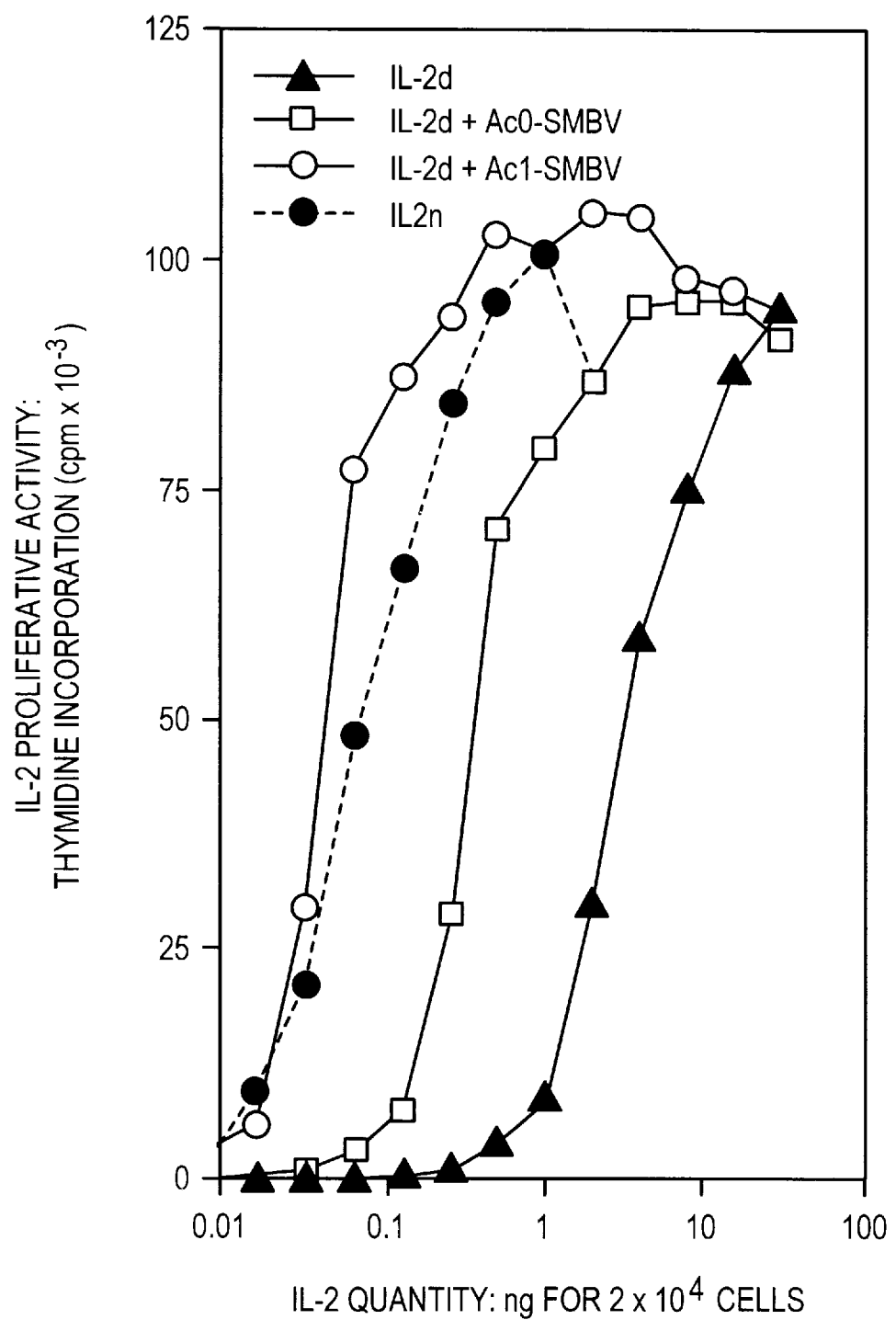

FIG. 14: Effect of the acylated cores on the restoration of the activity on cell proliferation of denatured IL-2. The continuous line and the squares represent the activity of the denatured IL-2, the circles the activity of the denatured IL-2 associated with the AC0 cores, the triangles the activity of the denatured IL-2 associated with the AC1 cores, and the dotted line represents the activity of native IL-2 on $2 \times 10^4$ CTLL cells.

EXAMPLE 1

Preparation of particles charged with IL-2

Interleukin-2 human recombinant (Genzyme), radio-labeled human recombinant ($^{35}S$ methionine and cysteine) prepared from recombinant BHK-21 cells, mouse recombinant (Genzyme).

Syntheses of the polysaccharide cores (PSC)

300 g of Waxylis 100 starch (Roquette, France) are dissolved in 2N sodium hydroxide and then 8 ml of epichlorohydrin are added. A gel is obtained which is neutralized with acetic acid and then washed with water. This gel is diluted in 2.25 l of 1.5N sodium hydroxide and then there are added 57 ml of $POCl_3$ at a flow rate of 9 ml/hour and 342 ml of 10N sodium hydroxide at a flow rate of 54 ml/hour. The gel is neutralized with acetic acid and ground with a Minilab high-pressure homogenizer. The suspension obtained is centrifuged for 15 minutes at 10,000 g; analysis of the supernatant using a nanosizer shows a homogeneous population of particles of 200 nm. These PSC are freeze-dried in the presence of ammonium hydrogen carbonate. The nonacylated polysaccharide cores are designated AC0.

Synthesis of the acylated nuclei (AC1, AC2 and AC3)

30 g of freeze-dried PSC are mixed with 450 ml of freshly distilled dichloromethane. 3.3 ml of palmitic acid chloride are added with stirring. After 2 hours of reaction, the reaction medium is filtered and washed with ethyl ether. The AC1s are then ultrafiltered and freeze-dried. The acylated nuclei obtained can undergo 1 to 2 acylation cycles identical to that described, this improving the homogeneity of the fatty acid crown on the outside of the particles. The size of the acylated particles remains constant at 200 nm. We obtain after one acylation cycle AC1s, 2 cycles AC2s, 3 cycles AC3s. These acylated nuclei are freeze-dried and used in freeze-dried form.

Association of IL-2 with the ACs

Depending on the experiments, variable quantities of IL-2 can be associated with the acylated or nonacylated polysaccharide cores. For 10 units of IL-2/ mg of AC, 0.5 mg of AC is hydrated directly with 200 µl of IL-2 previously diluted in PBS buffer (50 units/ml). After gentle stirring and allowing to stand for one hour at 4° C., the suspension is supplemented with 1 ml of cell culture medium.

Depending on the needs, the mixture is tested immediately or purified in order to separate the IL-2 which has not been associated with the ACs.

Separation of the IL-2 which has not been associated with the ACs

The IL-2/AC mixture is centrifuged (5 min at 2000 g). The supernatant (S) is carefully collected so as to be tested and the pellet (P: bound IL-2) is washed twice with medium and then resuspended in the supplemented culture medium.

Demonstration of the association of IL-2 with the acylated polysaccharide cores

The association of IL-2 with the polysaccharide cores and with the acylated polysaccharide cores is possible as shown by the results presented in Table 1 below, indeed since a clear decrease is recorded in the concentration of IL-2 contained in the supernatant. However, it is only with the acylated polysaccharide cores that the IL-2 was not able to be released after taking up the pellet containing the bound IL-2.

TABLE 1

Interaction between human recombinant interleukin-2 and the polysaccharide cores: importance of acylation.

| Nature of the product | Biological activity of IL-2 (Units per ml) After association with: | |
|---|---|---|
| | Polysaccharide cores | Acylated polysaccharide cores |
| Mixture* | 1.1 | 5 |
| Supernatant* | 0.3 | 0.4 |
| Pellet + PBS* | 0.5 | 2.7 |

Control IL-2: 1.4 units per ml

Human recombinant IL-2 was mixed either with the polysaccharide cores or with the acylated polysaccharide cores and centrifuged for part of the mixture after interaction on the day itself. After storing for 7 days at 4° C., the quantity of IL-2 present in each type of product was determined according to the Gillis method (J. Immunol. 1978, 120, 2027).

Mixture: IL-2/core mixture stored 7 days at 4° C.

Supernatant: IL-2 not associated with the cores and stored 7 days at 4° C.

Pellet+PBS: IL-2 associated with the cores and released during the 7-day storage.

The association of IL-2 with the polysaccharide cores is greater when they have been acylated. This is demonstrated by assaying the biological activity of the IL-2 contained in the interaction supernatant (5 hours) after removal of the acylated nuclei (AC). These results are presented in Table 2.

TABLE 2

Initial quantity of IL-2: 70 U

Content of IL-2 in the interaction supernatant with:

AC0: 30.0 U
AC1: 0.2 U
AC2: 0.2 U
AC3: 0.2 U with AC0, 50% of the IL-2 was associated with the AC or inactivated whereas with the acylated ACs, all the IL-2 was associated with the AC or inactivated.

The number of acylations does not appear here to influence the capture of IL-2.

The same type of result is obtained with radio-labeled IL-2 (Table 3).

TABLE 3

Demonstration of an association between radio-labeled IL-2 and the polysaccharide cores, acylated or otherwise.

| Nature of the polysaccharide cores | IL-2 not associated with the cores* | Time of controlling the release of the IL-2* associated with the cores | | |
|---|---|---|---|---|
| | | 12H | 24H | 96H |
| AC0 | 540 | 27 | 23 | 15 |
| AC1 | 160 | 41 | 28 | 13 |
| AC2 | 220 | 46 | 24 | 20 |
| AC3 | 130 | 36 | 24 | 20 |

*The results represent the cpm number per 20 µl.

Radio-labeled IL-2 (1700 cpm/20 µl) was used to hydrate the cores. After 5 hours of interaction, the mixture is centrifuged and the supernatant is controlled (non-associated IL-2). The centrifugation pellet is then resuspended in PBS for 7 hours and then centrifuged and controlled (12 H point). The new pellet is again resuspended in PBS for 12 hours (24 H point) and so on.

It can be observed that here also the acylation induces a greater association of IL-2. It appears that IL-2 associated with the cores is only very slightly released over time in the presence of buffer. However, in spite of the faintness of the radioactivity, it seems that the release of IL-2 is greater from the acylated structures.

EXAMPLE 2

Nature of the interaction of IL-2 with the cores

In order to determine the nature of the interaction between IL-2 and the cores, IL-2 bound to the cores was eluted with various solutions: PBS buffer, detergent solution (1% Hecameg) or 0.5M NaCl. As shown by the preliminary results presented in Table 4, no IL-2 is released with PBS whereas a large quantity is released with the detergent and very little or none with increase in the ionic strength. It therefore appears that the nature of the interaction between the IL-2 which has been released and the cores is hydrophobic rather than hydrophilic, including with the cores which have not been acylated.

TABLE 4

Demonstration of an association between IL-2 and the polysaccharide cores, acylated or otherwise: IL-2 (biological activity) released (12 hours of interaction) from ACs free of the initial IL-2.
Release of IL-2*

| Nature of the polysaccharide cores | Nature of the treatment of the cores after interaction with IL-2 | | |
|---|---|---|---|
| | PBS | 1% Hecameg | 0.5M NaCl |
| AC0 | 0 | + | +/− |
| AC1 | 0 | + | +/− |
| AC2 | 0 | + | + |
| AC3 | 0 | + | 0 |

*The results represent an optical reading of the proliferation of the CTLL cells.

The interactions between IL-2 and the acylated cores are very strong since little IL-2 is released during 23 days of storage at 4° C. In contrast, after this storage time, a high quantity of IL-2 can be released by a detergent/1% hecameg).

TABLE 5

Demonstration of an association between radio-labeled IL-2 and the cores: study of the type of major interaction between IL-2 and the cores.

| Nature of the polysaccharide cores | Release of IL-2 (cpm per 20 µl) from cores sedimented after 23 days and after treatment with: | | |
|---|---|---|---|
| | No supernatant | PBS | Hecameg |
| AC0 | 22 | 31 | 32 |
| AC1 | 28 | 25 | 283 |
| AC2 | 52 | 44 | 213 |
| AC3 | 72 | 52 | 329 |

EXAMPLE 3

Evaluation of the effect of the association of IL-2 with the ACs a) Materials and methods Murine CTLL cells (cytotoxic T lymphocyte line) whose survival and growth depend on the presence and the quantity of IL-2 are used as indicator cells. They are cultured in supplemented RPMI medium (glutamine, antibiotics, fetal bovine serum, sodium pyruvate, non-essential amino acids, Hepes and β-mercaptoethanol).

In 24-well plates, the samples (1 ml) are tested by adding them to 1 ml of CTLL cells, at $2 \times 10^5$ cells per ml. The plates are then incubated at 37° C. in a humid atmosphere and in the presence of 7% $CO_2$. Each day of the control, all the wells to be tested are collected and centrifuged. The supernatant is recovered and frozen in order to measure subsequently the IL-2 (residual IL-2). The cell pellet is resuspended in culture medium for enumeration of the live cells.

The growth of the cells is also tested based on their capacity to incorporate tritiated thymidine into their genome on the day of the control. To this end, in 96-well plates, 100 µl of sample are mixed with 100 µl of cells containing $2 \times 10^5$ cells per ml. On the day of the control, tritiated thymidine is added for 5 hours and the radioactivity is determined after lysis and filtration of the cells.

Methods of control

Enumeration of the live cells

The enumeration of the live cells is performed based on the level of incorporation of a vital stain (MTT) into the cultured cells.

Titration of IL-2

The IL-2 contained in the various products of association with the acylated cores or the residual IL-2 is assayed according to the usual technique (method of Gillis: proliferation).

b) Consequence of the association of IL-2 with the acylated cores on the proliferation of the IL-2 dependent cells When the IL-2/acylated polysaccharide core (batch 14) mixture is added to the CTLL cell culture medium, it is observed (FIG. 1) that the quantity of cells which have proliferated is higher than in the presence of the same concentration of IL-2 alone, in a form diluted in PBS. The same type of results is obtained with another batch of acylated polysaccharide cores (batch 18: FIG. 4).

Furthermore, if instead of enumerating the live cells, the capacity of the cells to proliferate in the culture is evaluated (incorporation of tritiated thymidine) (FIG. 2), the presence of the mixture of IL-2 and of acylated polysaccharide cores significantly increases this capacity. Not only is IL-2 which is still active on new cells present in the supernatants, but this IL-2 mixed with the acylated polysaccharide cores prolongs the proliferation of the cells. This presence of the mixture has two consequences (FIG. 3): 1) during the entire culture (except on day 10), the number of dead cells is lower in the presence of acylated polysaccharide cores; 2) the total number of cells at the end of the culture is greater in the presence of acylated polysaccharide cores.

c) Influence of the acylation of the polysaccharide cores on their capacity to enhance the properties of IL-2

In the absence of IL-2, the polysaccharide cores (PSC) as well as the acylated polysaccharide cores (AC) are not capable of inducing either the growth or the survival of the cells (FIG. 4). In contrast, the acylated polysaccharide cores enhance the properties of IL-2. On the other hand, the nonacylated polysaccharide cores have instead a negative effect on the growth of the cells (FIG. 4).

EXAMPLE 4

Influence of the degree of acylation and of the quantity of the IL-2/core mixture on the enhancement of the properties of IL-2

In a series of experiments, two quantities of the IL-2/core mixture were tested; 20 units of IL-2 were associated with the cores and optionally diluted 1/5 (the quantity of cores was thereby equally diluted). It is commonly checked that when large quantities of IL-2 are added to the indicator cells, this results in an inhibition of the growth of the cells. We checked that the initial conditions for interaction between IL-2 and the cores did not result from this case (FIG. 5): with 4 units, the cells proliferated less than with 20 units.

With 20 units of IL-2, it is observed that the growth of the cells (FIG. 6a) with IL-2 mixed with the cores is mainly increased with the cores which have undergone 2 or 3 acylations. The same type of results, but less pronounced, is obtained by measuring the capacity of the cells to proliferate (FIG. 6*b*).

With 4 units of IL-2, the results (FIGS. 7*a* and 7*b*) are more clear-cut: the acylation plays an important role as already demonstrated (FIG. 4). However, an increase in the acylation decreases the enhancement of the growth (FIG. 7*a*) as well as the proliferative capacity of the cells (FIG. 7*b*).

It is possible that the system is inhibited by an excessive activity of IL-2, for 20 U of IL-2.

Influence of the quantity of acylated cores on the enhancement of the properties of IL-2

The same quantity of IL-2 was mixed either with 2 mg or with 0.1 mg of acylated cores in order to study the influence of the quantity of cores on the enhancement of the properties of IL-2. As shown by the results presented in FIG. 8, it is especially on days 1 and 3 that the differences appear: the growth (FIG. 8*a*) and the proliferative capacity (FIG. 8*b*) are greater for the largest quantity of cores.

EXAMPLE 5

Consequence of the association of IL-2 with acylated or nonacylated cores on the presence of residual IL-2 in the culture supernatants of the CTLLs It appears that besides an enhancement of the specific activity of IL-2, a phenomenon of "protection" of IL-2 or of slow release of an active IL-2 could be observed in the case where the latter has been previously associated with the acylated polysaccharide cores. Several of these three hypotheses could even be brought about simultaneously. In order to clarify this point, in the various cell proliferation experiments, the residual IL-2 present was titrated at various culture times.

a) Influence of the acylation of the polysaccharide cores on the quantity of residual IL-2 in the cultures As shown by the results presented in FIG. 9 (same conditions as FIG. 4), more IL-2 is present in the culture supernatants having received the mixture of IL-2 with acylated cores, the presence of the mixture of IL-2 and of nonacylated cores having instead the effect of causing a decrease in the residual IL-2. However, from the beginning, the apparent residual quantity of IL-2 is substantially greater than that observed with the control IL-2 preparation, indicating that either IL-2 was protected better during the first 24 hours of culture or the specific activity of IL-2 was enhanced (improvement in the presentation of IL-2).

b) Influence of the degree of acylation and of the quantity of the IL-2/core mixture on the quantity of residual IL-2 in the cultures The residual IL-2 was also tested in the culture supernatants corresponding to FIGS. 6 and 7. As above, a very high residual quantity of IL-2 is recorded when the cores have undergone acylation, either with 20 or 4 units of IL-2. Just as for the proliferation, the increase in the activity of IL-2 is more significant in the presence of a lower quantity of IL-2 (20 U FIG. 10 and 4 U FIG. 11). Several acylations lead to a lower activity than that obtained with a single acylation.

c) Influence of the quantity of cores on the residual quantity of IL-2 in the cultures The residual quantity of IL-2 also depends on the quantity of acylated cores with which it has been associated, as shown by FIG. 12. Here again, the important role of the acylated cores is observed.

EXAMPLE 6

Demonstration of different biological properties between bound IL-2 and free IL-2

20 units of IL-2 are mixed with acylated cores (AC1) and then centrifuged. The pellet and the supernatant were tested separately for their ability to induce the growth of the cells (FIG. 13). It is observed, as above, that the IL-2/AC mixture enhances the properties of IL-2. The same is true for the IL-2 bound to the ACs. In contrast, the supernatant, here again, no longer contains enough IL-2 to induce proliferation.

EXAMPLE 7

Interaction between interleukin-2 and the biovectors: influence of acylation

The possibility of interaction of IL-2 with the acylated cores was determined. IL-2 is mixed with cores (acylated or otherwise), diluted in cell culture medium supplemented with 10% FBS (fetal bovine serum), incubated at 37° C. and tested at defined times for its activity on the proliferation in a mixture with the vectors or after their removal.

The supernatants corresponding to the IL-2/vector mixtures show a significant decrease in the activity on proliferation immediately after the removal of the polymers, compared with the activity of IL-2 alone. Only 15% and 70% of the IL-2 activity is recovered with the AC2 and AC0 cores respectively. The IL-2 associated with the vectors is still active because the resuspended pellets can induce the growth of the CTLL cells up to 4 days after they have been added to the CTLL cells. This data strongly suggests that IL-2 is associated with the vectors because it is removed during the centrifugation. In addition, the activity on the proliferation of IL-2 is preserved up to day 4, with a maximum of two days after its association with the vectors.

As regards the stability of IL-2, after two days, the activity on the proliferation of IL-2 alone decreases very strongly whereas a significant proliferation can still be demonstrated with IL-2 after interaction with AC0 or AC1 cores. This may suggest that the IL-2 associated with the vectors is gradually released under the cell culture conditions. The release of IL-2 is greater for the AC0 and AC1 cores.

The activity on the proliferation of IL-2 mixed with vectors is also measured after storing at 37° C. The increase in the activity of IL-2 is demonstrated when IL-2 has been incubated with vectors regardless of the day of control. The greatest effect is observed after 24 hours with the AC2 cores.

Under these conditions, the nonacylated cores slightly increase the activity of IL-2 in contrast to what was observed in the preceding experiments. This difference can be explained by a slow association of IL-2 with the AC0 cores, compared with the acylated cores. After two days of culture, the activity of IL-2 decreases gradually, probably both because of the denaturation and of the release.

These results show clearly that IL-2 may be associated with the vectors (more efficiently when they are acylated) and that the IL-2 associated with the vectors has an activity on proliferation; the IL-2 associated with the particulate vectors may be released in an active form.

EXAMPLE 8
Restoration of the activity on the proliferation of a denatured IL-2 by association with the particulate vectors according to the invention Purified recombinant human IL-2 produced by yeast (Genzyme Corp) is denatured or aggregated by reconstitution and dilution in PBS buffer followed by freezing at $-20°$ C. and then thawing. Under these conditions, a 50% response is obtained with about 40 ng/ml (or 4 ng per $2\times10^4$ CTLL cells) instead of about 0.8 ng/ml (or 0.08 ng per $2\times10^4$ CTLL cells) for the preparation of native IL-2, as shown in FIG. 14. This high decrease in the activity of IL-2 (50 to 100 times less) confirms that the treatment with PBS and freezing/thawing reduces the bioavailability of IL-2.

The denatured IL-2 is also incubated with acylated cores. This treatment partially or completely restores the activity of IL-2 in this preparation when it is mixed with AC0 or AC1 cores respectively. After association with the AC0 or AC1 cores (as well as with AC2 or AC3 cores) about 10 to 100 times less IL-2 is respectively necessary to induce the same level of proliferation as with IL-2 alone. After association with acylated cores, the activity of IL-2 on proliferation is the same or greater than that before denaturation. Consequently, besides their effect on nondenatured IL-2, the vectors according to the invention can restore the activity of denatured IL-2 on proliferation in vitro. This restoration is more marked when the vectors are acylated.

EXAMPLE 9
Influence of the origin of the IL-2 on the capacity of the acylated polysaccharide cores to enhance the properties of the IL-2

Besides human recombinant IL-2 (Hr IL-2), rat IL-2 was associated with the acylated polysaccharide cores. The same enhancement phenomenon is observed, as indicated in Table 6.

TABLE 6

Influence of the origin of the IL-2 on the capacity of the acylated polysaccharide cores to enhance the properties of the IL-2 in relation to the proliferation of the cells (control on day 3).

| Nature of the product | Proliferation of the cells (cpm $10^{-3}$) | |
|---|---|---|
|  | Not associated | Associated with the acylated cores |
| Hr IL-2 | 11 | 31 |
| rat IL-2 | 17 | 83 |
| rat IL-2 1/10 | 1 | 2 |

We claim:

1. Particulate vector comprising, from the inside to the outside,
    a nonliquid organic hydrophilic core, and
    an external layer consisting of lipid compounds, having an activatable functional group, grafted on the core by covalent bonds.
2. Particulate vector according to claim 1, wherein the core consists of a matrix of naturally or chemically cross-linked polysaccharides or oligosaccharides.
3. Particulate vector according to claim 1, wherein ionic ligands are grafted onto the core, and the core has a ionic character.
4. Vector according to claim 3, wherein ionic ligands carry at least one functional group selected from the group consisting of phosphates, sulfates, carboxylic acids, quaternary ammoniums, tertiary amines, and primary amines.
5. Particulate vector according to claim 1, wherein the lipid compounds of the external layer are natural fatty acids bound to the core at a variable level.
6. Particulate vector according to claim 1, which is in freeze-dried form.
7. Particulate vector according to claim 1, further comprising molecules of at least one cellular mediator having both a hydrophobic character and an ionic character, of the type which acts via a membrane receptor, and said molecules are associated by hydrophobic interactions with the external layer of lipid compounds of the vector, and/or by ionic interactions with the core.
8. Particulate vector according to claim 7, wherein the molecules of cellular mediators are polypeptides which play a role in the functioning of the immune system.
9. Particulate vector according to claim 7, wherein the molecules of cellular mediators are cytokines selected from the group consisting of interleukins, interferons, TNFs, G-CSF, M-CSF, GM-CSF and MIF.
10. Particulate vector according to claim 9, wherein the cytokine is interleukin-2.
11. Pharmaceutical composition comprising particulate vectors according to claim 1 in a pharmaceutically acceptable vehicle.
12. Process for enhancing the activity of a polypeptide cellular mediator which is at least partially hydrophobic comprising
    a) preparing a particulate vector which comprises from the inside to the outside
       a organic core consisting of a matrix of naturally or chemically cross-linked polysaccharides or oligosaccharides, an external layer consisting of natural fatty acids grafted onto the core by covalent bonds, at a variable level, b) optionally, preparing an aqueous suspension of said particulate vector, and freeze drying the vector obtained in a hydrophilic environment, and c) associating the cellular mediator with the vector via interactions which are at least partially hydrophobic.

13. Process for enhancing the activity of a cellular mediator comprising a) preparing a particulate vector comprising a cross-linked hydrophilic organic core onto which fatty acid residues and ionic ligands are grafted, b) preparing an aqueous suspension of said particulate vector, c) freeze-drying said particulate vector, d) placing the freeze-dried vector in contact with an aqueous solution of cellular mediator, so as to bring about the formation of stable aggregates of vectors charged with cellular mediator.

14. A particulate vector comprising:

a nonliquid, organic hydrophilic core comprising polysaccharides, and an external lipid layer, wherein said lipids have a functional group which reacts with said polysaccharide core, grafted on the core by covalent bonds.

15. A pharmaceutical composition comprising particulate vectors according to claim 14 in a pharmaceutically acceptable vehicle.

16. A process for enhancing the activity of a polypeptide cellular mediator which is at least partially hydrophobic comprising a) preparing a particulate vector according to claim 14, b) optionally, preparing an aqueous suspension of said particulate vector and freeze-drying the vector obtained in a hydrophilic environment, and c) associating the cellular mediator with the vector via interactions which are at least partially hydrophobic.

17. A process for enhancing the activity of a cellular mediator comprising a) preparing a particulate vector according to claim 14, b) preparing an aqueous suspension of said particulate vector, c) freeze-drying said particulate vector, d) placing the freeze-dried vector in contact with an aqueous solution of cellular mediator, so as to bring about the formation of stable aggregates of vectors charged with cellular mediator.

18. The particulate vector of claim 1, wherein said lipid compounds have an acylatable functional group.

* * * * *